(12) United States Patent  
Ries et al.

(10) Patent No.: US 7,769,458 B2
(45) Date of Patent: *Aug. 3, 2010

(54) SMALL FORMAT CONNECTOR CLIP OF AN IMPLANTABLE MEDICAL DEVICE

(75) Inventors: Andrew J. Ries, Lino Lakes, MN (US); Jay Lahti, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 87 days.

This patent is subject to a terminal disclaimer.

(21) Appl. No.: 10/632,058

(22) Filed: Jul. 31, 2003

(65) Prior Publication Data

US 2005/0027327 A1 Feb. 3, 2005

(51) Int. Cl.
*A61N 1/375* (2006.01)
(52) U.S. Cl. ........................................ 607/37
(58) Field of Classification Search .............. 607/37, 607/36; 439/909, 827, 335, 668
See application file for complete search history.

(56) References Cited

U.S. PATENT DOCUMENTS

| | | | |
|---|---|---|---|
| 4,445,511 A * | 5/1984 | Cowdery et al. | 607/37 |
| 4,655,462 A | 4/1987 | Balsells | |
| 4,848,346 A * | 7/1989 | Crawford | 607/37 |
| 5,275,620 A | 1/1994 | Darby et al. | 607/1 |
| 5,413,595 A | 5/1995 | Stutz, Jr. | 607/637 |
| 5,730,628 A | 3/1998 | Hawkins | |
| 5,769,671 A * | 6/1998 | Lim | 439/843 |
| 6,498,952 B2 | 12/2002 | Imani | |
| 2004/0093038 A1* | 5/2004 | Biggs et al. | 607/37 |
| 2005/0027325 A1* | 2/2005 | Lahti et al. | 607/37 |
| 2005/0027326 A1* | 2/2005 | Ries et al. | 607/37 |

FOREIGN PATENT DOCUMENTS

EP 0 590 756 A2 6/1994

OTHER PUBLICATIONS

Merriam-Webster Online Dictionary, (http://www.webster.com); searched: flange.*

* cited by examiner

*Primary Examiner*—George R Evanisko
*Assistant Examiner*—Alyssa M Alter
(74) *Attorney, Agent, or Firm*—Stephen W. Bauer

(57) ABSTRACT

A connector assembly for detachably connecting an electrical lead to an implantable medical device for emitting electrical pulses is provided. One or more deflectable connector clips are positioned inside or partially inside a compact housing that is designed to deflect the connector clips in a partially loaded state so that insertion of the terminal pin of an electrical lead causes a minor deflection of the spring clip, but results in high retention force. The positioning of the connector clip in the housing in a partially loaded state results in a relatively flat force deflection curve. The one or more connector clips are preferably electrically conducting metal and may be formed into a U-shape. The connector clips are generally positioned to provide multiple contact points with an inserted terminal pin of a lead.

23 Claims, 7 Drawing Sheets

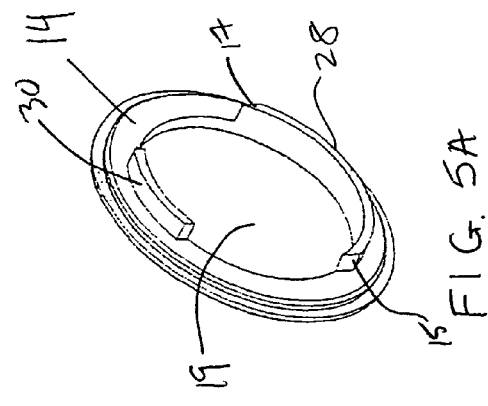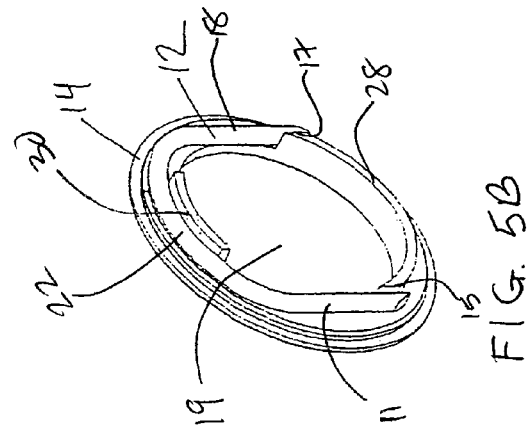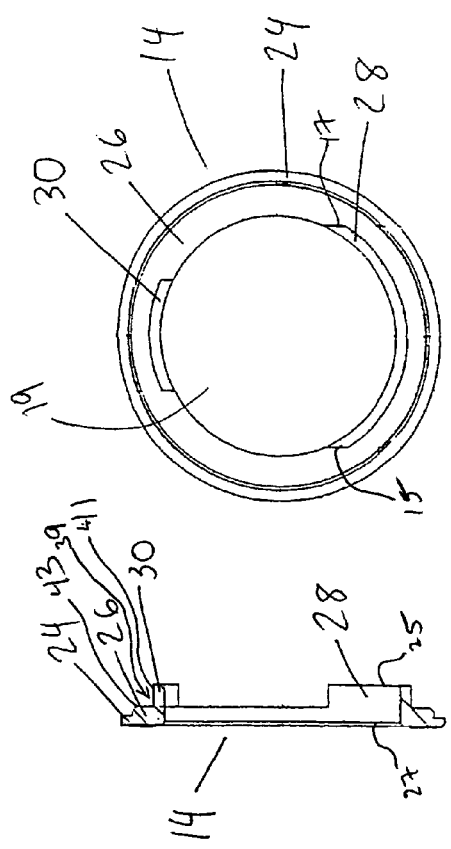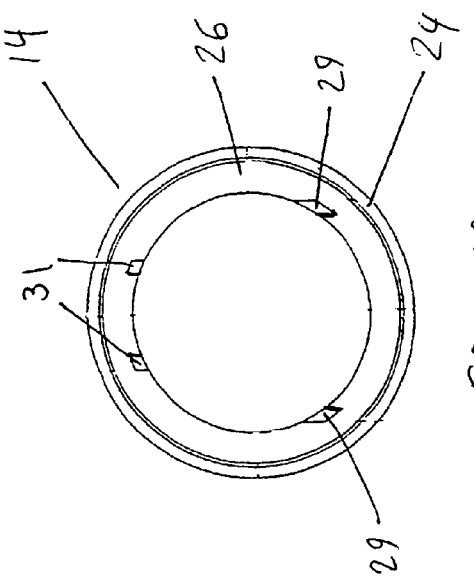

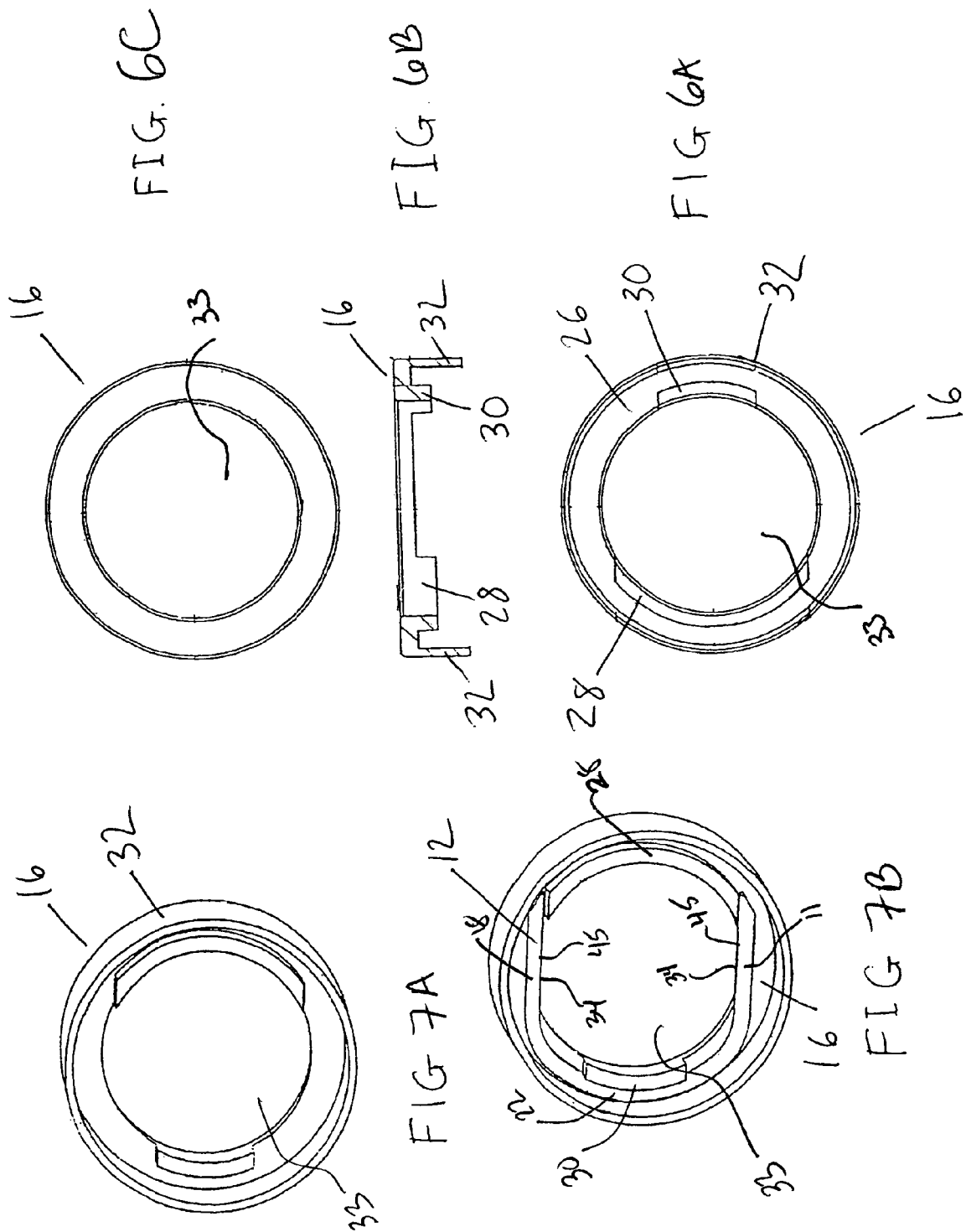

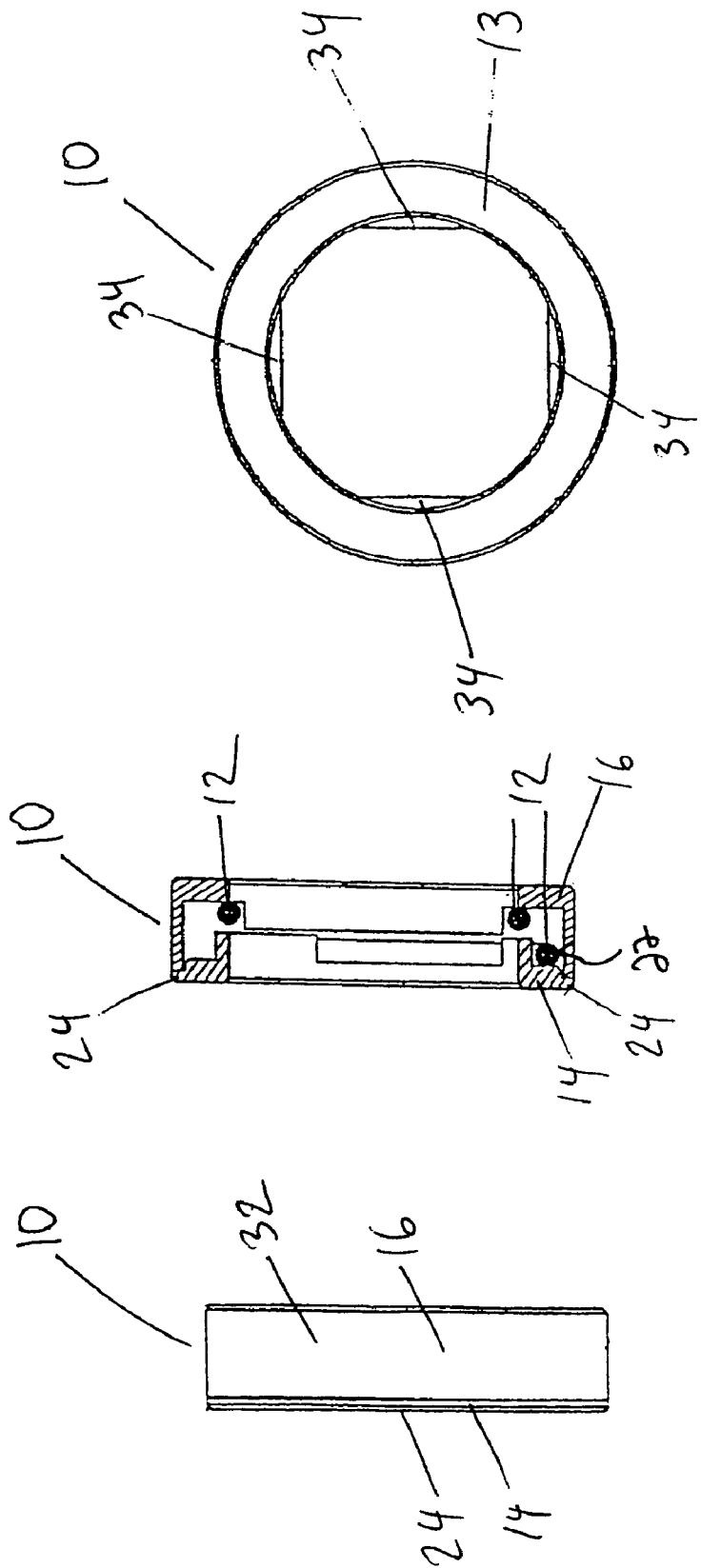

SMALL FORMAT CONNECTOR CLIP OF AN IMPLANTABLE MEDICAL DEVICE

CROSS-REFERENCE TO RELATED APPLICATIONS

Cross-reference is hereby made to commonly assigned related U.S. applications, filed concurrently herewith, entitled "CONNECTOR ASSEMBLY FOR CONNECTING A LEAD AND AN IMPLANTABLE MEDICAL DEVICE", entitled "CONNECTOR ASSEMBLY FOR CONNECTING A LEAD AND AN IMPLANTABLE MEDICAL DEVICE", entitled "ELECTRICAL CONNECTOR ASSEMBLY FOR COUPLING MEDICAL LEADS TO IMPLANTABLE MEDICAL DEVICES", incorporated herein by reference in their entirety.

FIELD OF THE INVENTION

The present invention relates generally to implantable medical devices, and more particularly to a compact electrical connector that makes efficient use of axial space within the connector cavity of an implantable medical device.

DESCRIPTION OF THE RELATED ART

Implantable medical devices are in use to provide electronic pulses to stimulate tissue via a lead extending from an implanted pulse generator to an internal target site. A common example of this type of technology is a pacemaker and a pacing lead that provides electrical stimulation for the heart. Pacemakers are usually implanted in a subcutaneous cavity, and their leads extend either to the internal cavities of the heart or to patch electrodes located along an external surface of the heart.

In many pacemakers known in the art, the distal portion of the pacemaker lead is made up of one or more electrodes that are placed within the target tissue. Electrical signals are sent along the lead, both pacing pulses from the pacemaker to the heart, and usually feedback physiological signals from the heart to the pacemaker as well. A terminal pin is usually affixed to the proximal end of the lead that is designed to establish an electrical connection between the implanted pulse generator and the pacing lead. The terminal pin is normally inserted into a socket in the connector cavity area of the pacemaker, where it establishes a connection through an electrical connector. The electrical connector in such pacemaker embodiments serves as an important interface between the pacing lead and electronic circuitry within the pacemaker. Therefore, it is imperative that the electrical connection between the terminal pin and the connector provide a reliable, long-term, safe and secure, yet readily detachable connection.

Various connectors have been used to connect the terminal pin of the lead to the electrical connector in the socket of a pacemaker. A common connector system uses a miniature socket head set screw to secure the terminal pin to the electrical connector inside the socket thereby providing the necessary electrical contact. When this type of connector system is employed, a physician must tighten the set screw after the terminal pin of the lead is in place within the pacemaker during implantation of the device. The set screw is normally torqued at about 14 inch-ounces to adequately secure the terminal pin of the lead. This procedure is usually very difficult due to the small size of the screw and the inconvenient working conditions of the operating room.

A number of problems arise from the use of the set screw. One is that the set screw sometimes protrudes into the core of the connector before the lead is inserted. When this occurs, the physician attempting to attach the lead may attempt to force the lead into the blocked bore, resulting in frustration and possible damage to the device. In addition, if the set screw is overtorqued during attachment of the lead, the screw socket or threads may be stripped thereby causing potential failure of the set screw and difficulty in later attempts to remove the set screw.

Another problem that may result from overtightening the set screw is that the screw may excessively bear against the outer ring of the lead terminal. Such bearing against the outer ring may cause the ring to deform and thereby preventing the removal of the lead from the connector socket. If the lead cannot be removed from the connector socket upon failure of the pacemaker both the lead and pacemaker may have to be removed from the patient when replacement of the pacemaker alone would normally be desired. Alternatively, it may be necessary to cut the leads so that the pacemaker can be removed. Of course the cutting of the leads requires the reattachment of the cut ends to either the pacemaker directly or to another lead thereby leaving an additional connection point that may be subject to failure.

Finally, problems may develop in utilizing a set screw when a wrench is inserted to rotate the set screw. The opening of the set screw may allow bodily fluids to enter the connector through the threaded bore when the screw is in an open or partially opened position. The entry of bodily fluids through the threaded bore may lead to deterioration of the connection site over time.

Several attempts have been made to provide a small electrical connector that avoids the problems discussed. One such device is the coiled spring connector described in U.S. Pat. No. 4,655,462 issued to Balsells. An alternative to the Balsells spring connector is a connector system employing various types of spring contacts in the form of small fingers, or cantilever beams, which contact the lead terminal pin. An example of this type of connector is provided by U.S. Pat. No. 5,730,628, issued to Hawkins. These known connectors have two basic disadvantages. First, such connectors may provide poor mechanical contacts between the terminal pin of the lead and the springs, resulting in a suboptimal intermittent electrical contact. Second, these connectors also must be dimensioned length and widthwise so as to be of sufficient size to allow the spring to deflect to effect the desired connection. This results in a long and wide connector that does not make efficient use of axial space within the connector cavity of the electrical impulse generator.

Another type of known electrical connector is a circular spring type connector described in U.S. Pat. No. 4,848,346, issued to K. F. Crawford. Disadvantages of this system are a relatively weak connection, and the need for buttons, which create potential failure points in the device.

Several other electrical connectors have been designed that make use of shape-memory metal to create a connection upon change of temperature. One such connector is disclosed in U.S. Pat. No. 6,498,952 issued to Imani et al. One disadvantage of this device is that the contact points are reduced relative to many connectors and the strength of the connection may be relatively weak. Furthermore, as with all shape-memory alloys, different temperatures must be provided for proper functioning, thereby creating uncertainty in the functioning of the connector.

BRIEF DESCRIPTION OF THE DRAWINGS

It is to be understood that the foregoing general description and the following detailed description are exemplary and explanatory but are not to be restrictive of the invention. The accompanying drawings which are incorporated in and constitute a part of this invention, illustrate one or more of the embodiments of the present invention, and together with the description, serve to explain the principles of the invention in general terms. Additionally, other features which are considered as characteristic for the invention are set forth in the appended claims. Advantages and features of the present invention will be readily appreciated as the same becomes better understood by reference to the following detailed description when considered in connection with the accompanying drawings, in which like reference numerals designate like parts throughout the figures thereof and wherein:

FIG. 4A is a top view of a female member of a housing of a connector assembly, according to the present invention;

FIG. 4B is a side view of the female member of FIG. 4A;

FIG. 4C is a top view of a female member of a housing of a connector assembly, according to an alternate embodiment of the present invention;

FIG. 5A is a perspective view of a female member of a housing of a connector assembly according to an embodiment of the present invention;

FIG. 5B is a perspective view of the female member of FIG. 5A having a connector clip positioned thereon;

FIG. 6A is a top view of a male member of a connector assembly, according to an embodiment of the present invention;

FIG. 6B is a side view of a male member of a connector assembly, according to an embodiment of the present invention;

FIG. 6C is a bottom, or exterior, view of a male member of a connector assembly, according to an embodiment of the present invention;

FIG. 7A is a perspective view of a male member of a connector assembly, according to an embodiment of the present invention;

FIG. 7B is a perspective view of the male member of FIG. 7A having a connector clip positioned therein;

FIG. 8A is a side view of an embodiment of an assembled connector assembly, according to the present invention;

FIG. 8B is a cross-sectional side view of the assembled connector assembly of FIG. 8A;

FIG. 8C is a top view of an assembled connector assembly, according to the present invention;

FIG. 9 is a schematic diagram of a connector assembly according to the present invention inserted within a connector cavity and having a lead connector positioned there through.

DETAILED DESCRIPTION OF THE INVENTION

The present invention relates to an improved connector assembly for detachably connecting and retaining the terminal pin of an electrical lead to an implantable medical device. The invention utilizes one or more resilient connector clips that are retained by an enclosing housing in a partially deflected configuration, or partially loaded state, such that a relatively constant force is exerted over the full range of deflection of the spring. Since only a small deflection of the spring is necessary to create significant force of retention on the inserted terminal pin of the lead, the connector assembly of the present invention allows for ease in inserting the terminal pin of the lead and allows for sufficient force to be exerted on the terminal pin for optimum retention of the lead without damaging it. Furthermore, the connector assembly of the present invention makes efficient use of the axial space on the terminal pin, allowing it to be very compact. Axial space is efficiently used due to the alignment of the spring contact perpendicular to the inserted lead. The connector readily accepts insertion of a terminal pin, without the use of tools, and applies a relatively even force through the connector clips to maintain a constant electrical contact with the electrical lead that is not subject to varying impedance. The connector of the present invention provides the requisite mechanical and electrical connection functions, using fewer components and less labor in implementation, yet providing higher reliability, durability, resistance to breakdown due to reactions with body fluids, a small size, and efficiency in manufacture.

Figure 1:
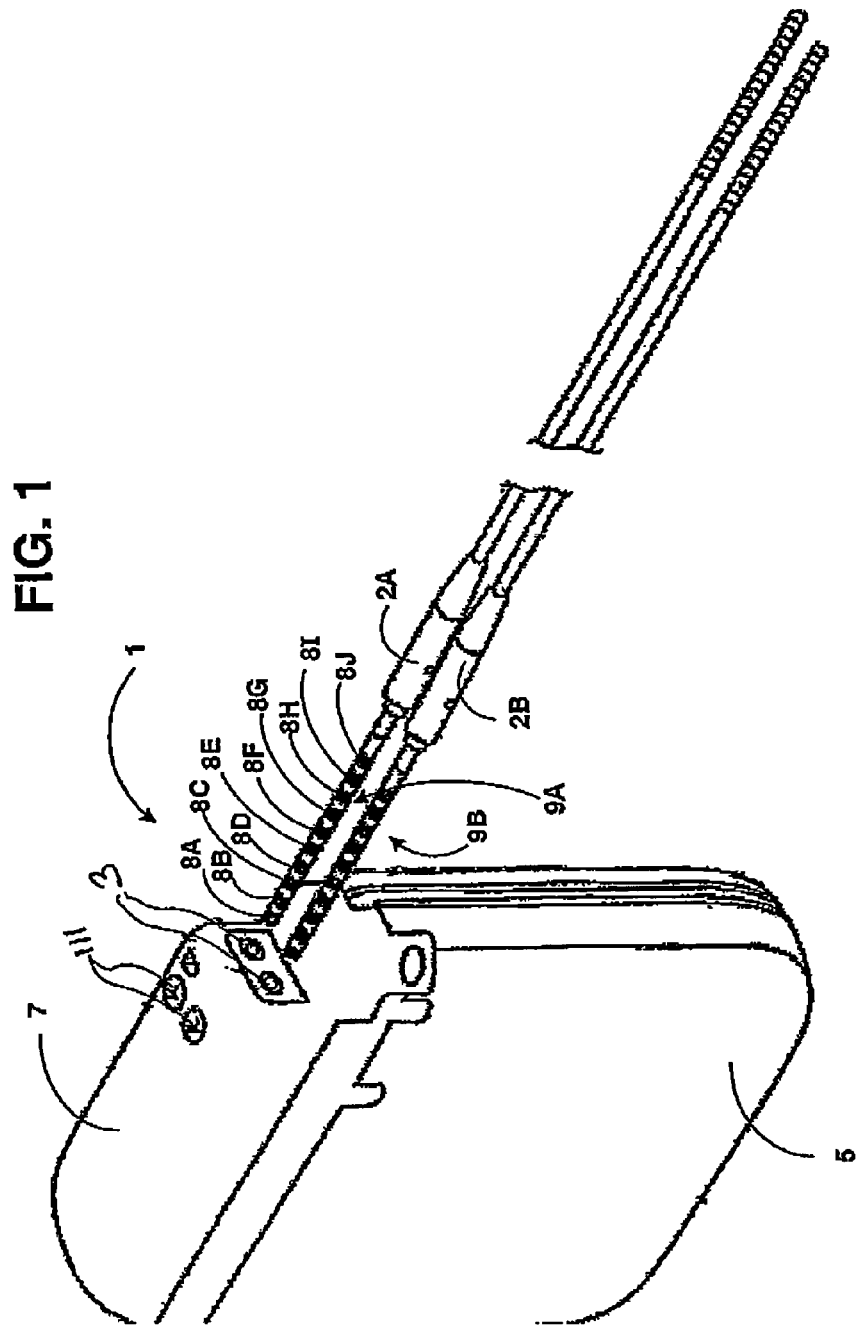
FIG. 1 is a perspective view of an exemplary implantable medical device capable of incorporating a connector assembly according to the present invention.

FIG. 1 is a perspective view of an exemplary implantable medical device capable of incorporating a connector assembly according to the present invention. As illustrated in FIG. 1, an exemplary implantable medical device (IMD) 1 incorporating a connector assembly according to the present invention includes a hermetically sealed, biologically inert housing 5, or "can", that houses IMD circuitry, one or more leads 2A, 2B that can be implanted in a patient, and a connector block 7 that receives proximal ends 9A, 9B of leads 2 to couple leads 2 to the circuitry in housing 5 as leads 2 are inserted within a connector port 3 formed in connector block 7. Once fully inserted within connector block 7, leads 2 are further fixedly positioned within connector block 7 by tightening positioning screws 111 against leads 2.

As illustrated in FIG. 1, the proximal ends 9A and 9B of lead 2A and 2B include a plurality of electrical contact areas 8A-8J (collectively contact areas 8). The present invention facilitates electrical coupling to one or more of contact areas 8 within connector block 7. Moreover, the present invention improves such contact for inline configurations like FIG. 1 in which a plurality of electrical contact areas 8 are positioned axially along a length of leads 2. In particular, the present invention allows size reductions of contact areas 8 by improving electrical coupling clips, described below, that electrically interface with contact areas 8 inside connector block 7.

IMD 1 corresponds to any medical device that includes medical leads and circuitry coupled to the medical leads. By way of example, IMD 1 takes the form of an implantable cardiac pacemaker that provides therapeutic stimulation to the heart. Alternatively, IMD 1 may take the form of an implantable cardioverter or an implantable defibrillator, or an implantable cardiac pacemaker-cardioverter-defibrillator. IMD 1 may deliver pacing, cardioversion or defibrillation pulses to a patient via electrodes disposed on distal ends of leads 2. In other words, leads 2 position electrodes with respect to various cardiac locations so that IMD 1 can deliver pulses to the appropriate locations.

Alternatively, IMD 1 corresponds to a patient monitoring device, or a device that integrates monitoring and stimulation features. In those cases, leads 2 include sensors positioned along distal ends of the respective lead for sensing patient conditions. The sensors include, for example, electrical sensors, electrochemical sensors, pressure sensors, flow sensors, acoustic sensors, optical sensors, or the like. In many cases, IMD 1 performs both sensing and stimulation functions.

In still other applications, IMD 1 corresponds to a neurological device such as a deep-brain stimulation device or a spinal cord stimulation device. In those cases, leads 2 are stereotactically probed into the brain to position electrodes for deep brain stimulation, or into the spine for spinal stimulation. In other applications, IMD 1 provides muscular stimulation therapy, blood sensing functions, and the like. In short, IMD 1 corresponds to any of a wide variety of medical devices that implement leads and circuitry coupled to the leads.

As outlined in detail below, connector block 7 of the present invention incorporates various components that improve and simplify electrical coupling between leads 2 and circuitry in housing 5. More specifically, an electrical connector clip provides a conductive interface between a medical lead and IMD circuitry. In addition, various components that assemble with the connector clip to form at least a portion of connector block 7 of IMD 1 are also described. For example, an improved structure having a channel for mating with one or more of leads 2 is designed for use with the connector clip so that biasing of the connector clip can be achieved prior to insertion of one or more leads 2 into the channel. As described below, such biasing allows for ease of insertion of one or more of leads 2 into the channel of the structure that forms at least part of connector block 7. In other words, the connector clip defines a desired amount of insertion force for lead pins inserted into connector block 7.

Figure 2:
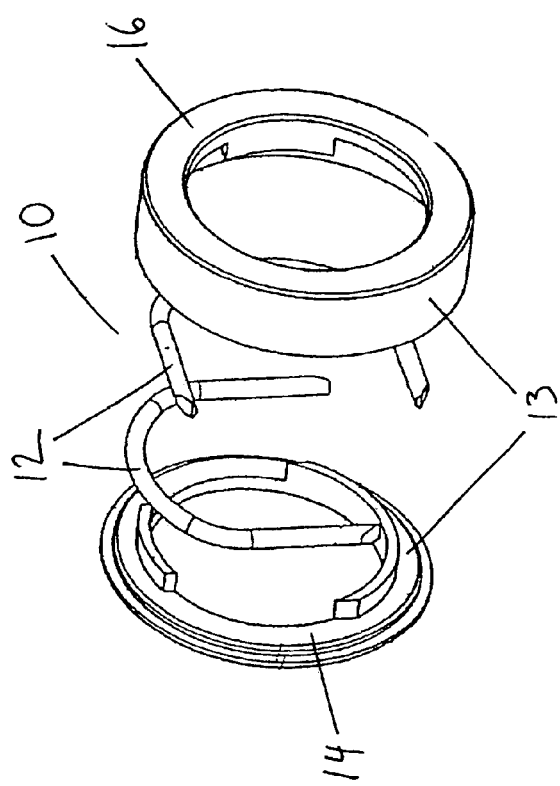
FIG. 2 is an exploded view, in perspective, of one embodiment of a connector assembly according to the present invention.

FIG. 2 is an exploded view, in perspective, of one embodiment of a connector assembly according to the present invention. In the embodiment shown in FIG. 2, a connector assembly 10 includes one or more connector clips 12 and a housing 13 including a female member 14, and a male member 16. Connector clips 12 are resilient and electrically conductive, while housing 13 is sealable and electrically conductive. Furthermore, housing 13 provides a structure that retains connector clips 12 in a partially deflected or partially loaded state and includes a suitable aperture for insertion of an electrical lead.

Figure 3:
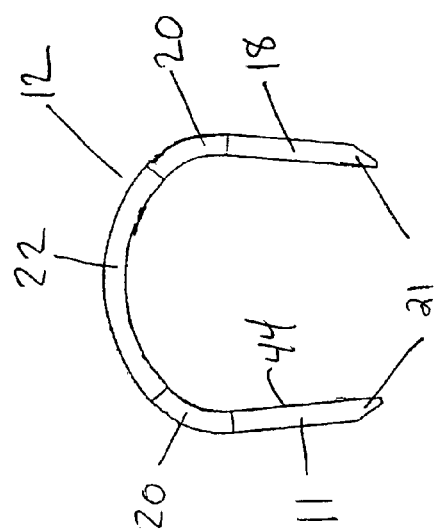
FIG. 3 is a plan view of a connector clip utilized in a connector assembly of the present invention.

FIG. 3 is a plan view of a connector clip utilized in a connector assembly of the present invention. As illustrated in FIG. 3, connector clip 12 is may be used to provide a means of retaining a lead (not shown) in place, or both functions together as a means of conducting electricity between contact areas 8 of a terminal pin of the lead and an electrical apparatus such as a pacemaker. Connector clip 12 is preferably prepared from a resilient, high strength, corrosion resistant, biocompatible material, such as tempered stainless steel. However, other materials suitable for such applications may be utilized in forming connector clip 12 employed in the present invention. Connector clip 12 may be stamped or cut from a sheet metal strip or cut and formed from wire stock. Connector clip 12 resembles a wire in form, and may be prepared with a number of differing cross-sections, such as circular or oval, for example, where a cross-section is created by a plane cutting perpendicular to the long axis of the wire. In an embodiment of the present invention, as illustrated in FIG. 3, connector clip 12 has an overall U-shape with an inner surface 44. However, it is noted that the connector clip could be configured in a variety of shapes including but not limited to square or diamond shape. Connector clip 12 generally includes a first spring arm 11 and a second spring arm 18, each including spring shoulders 20, and a spring back 22 extending between shoulders 20 of first arm 11 and second arm 18. Spring arms 11 and 18 are preferably bent or project inwards slightly, so that the distance between the ends of spring arms 11 and 18 is less than the distance between spring shoulders 20 when connector clip 12 is in a non-deflected state, as illustrated in FIG. 3.

The dimensions of the various sections of connector clip 12 may vary widely depending upon the size of the lead and the size of the cavity included in the electrical apparatus. However, connector assembly 10 when included within a pacemaker device, for example, will generally include connector clip 12 wherein the distance between ends of spring arms 11 and 18 is approximately 0.05-0.25 inches, the distance between spring arm 11/spring shoulder 20 at a widest point is approximately 0.075"-0.30", the distance between a line tangential to bottom of spring back 22 and an end of spring arm 118 is approximately 0.70-0.275 inches, a radius of curve along spring shoulders 20 is approximately 0.015-0.55 inches and a radius of curve along spring back 22 is approximately 0.05-0.10 inches". For example, the dimensions for one embodiment of connector clip 12 are as follows: a distance between ends of spring arms 11 and 18 is approximately equal to 0.107 inches; a distance between spring arm 11/spring shoulder 20 at a widest point is approximately equal to 0.20 inches; a distance between a line tangential to a bottom of spring back 22 and an end of spring arm 11 is approximately equal to 0.14 inches; a radius of curve along spring shoulder 20 is approximately equal to 0.035 inches; and a radius of curve along spring back 22 is approximately equal to 0.073 inches.

In various embodiments of the present invention the distal ends of spring arms 11 and 18 are preferably truncated on their outer edge to form wedges 21, as illustrated in FIG. 3. Wedges 21 are positioned on the ends of spring arms 11 and 18 to provide clearance between the ends of spring arms 11 and 18 and the sides of housing 13. Connector clip 12 having the dimensions provided above, when installed in a suitable housing (as described below), provides a contact that conforms with the proposed IS-4 standards, but could be reconfigured for IS-1 standards or other pin diameters within these ranges.

As previously mentioned, connector assembly 10 according to the present invention also includes housing 13 for supporting and retaining connector clip 12. FIG. 4A is a top view of a female member of a housing of a connector assembly, according to the present invention. FIG. 4B is a side view of the female member of FIG. 4A. FIG. 4C is a top view of a female member of a housing of a connector assembly, according to an alternate embodiment of the present invention. As illustrated in FIGS. 4A and 4B, according to an embodiment of the present invention, female member 14 is an annular disk with a wide, circular central aperture 19 centered within the annular disk. Aperture 19 is generally of sufficient size to accept proximal ends 9A, 9B of leads 2. Therefore, embodiments of the present invention include aperture 19 having a diameter of approximately 0.05-0.25 inches. In one embodiment, aperture 19 has a diameter of approximately 0.10-0.15 inches.

In the embodiment depicted in FIG. 4A, an outer rim of female member 14 forms an annular shelf 24, with reduced thickness relative to the rest of female member 14. When male and female members 14 and 16 are placed together, male member 16 rests over annular shelf 24 of female member 14, as shown in FIG. 8B. In various embodiments, annular shelf 24 extends approximately 0.002-0.020 inches radially outward from an edge of a main surface 26 of female member 14. In some embodiments, annular shelf 24 may be a quarter to three quarters the thickness of main surface 26.

Additionally, as illustrated in FIGS. 4A and 4B, female member 14 includes a bracing ridge 28 positioned along a lower half of female member 14 between main surface 26 and circular aperture 19. Bracing ridge 28 extends adjacent to an outer edge of central aperture 19 and an inner edge of main surface 26 to form a lower portion of aperture 19. In various embodiments of the present invention, bracing ridge 28 measures approximately 0.05-0.25 inches linearly from a first end 15 to a second end 17. In one embodiment of the present invention, bracing ridge 28 has a relatively flat arch shape, with a rectangular cross-section, and may be approximately 0.005-0.020 inches thick from a top portion 25 to a bottom portion 27 in a preferred embodiment as depicted in FIGS. 4A and 4B. Top portion 25 of bracing ridge 28 extends outward from main surface 26 to deflect spring arms 11 and 18 so that they remain in a partially loaded or deflected position when connector clip 12 is positioned within female member 14. Thus, when this embodiment of female member 14 is used to hold connector clip 12 with the dimensions described above, bracing ridge 28 deflects spring arms 11 and 18 from a resting separation of approximately 0.005 to 0.020 inches when in the non-deflected position, for an overall deflection of approximately 0.006-0.021 inches. It is noted that the dimensions identified in this embodiment may be increased or decreased depending upon the desired design of the connector in view of the size of the terminal pin of the lead. Furthermore, it is noted that in another embodiment of the present invention, illustrated in FIG. 4C, bracing ridge 28 may alternatively include two bracing pegs 29 extending outward from main surface 26 for separating spring arms 11 and 18 and placing connector clip 12 in a partially loaded or deflected position.

Depicted in FIGS. 4A and 4B, opposite from bracing ridge 28 and within female member 14, is a support ridge 30. As with bracing ridge 28, support ridge 30 may be a relatively flat arch that runs along the inner edge of main surface 26 and adjacent to the outer edge of circular aperture 19. In certain embodiments of the present invention, support ridge 30 extends outward from main surface 26 to approximately the same height as bracing ridge 28, but has a length of approximately one half of that of bracing ridge 28, so that the linear measurement from a first end 35 to a second end 37 of ridge 30 is approximately 0.01-0.15 inches. Alternatively, as depicted in FIG. 4C, support ridge 30 may include support pegs 31 extending outward from main surface 26, similar to bracing ridge 28, as described above. Support ridge 30 serves to anchor connector clip 12 in place by resting within the interior of spring back 22. Preferably, a cut out portion 39 formed by a side wall 41 between support ridge 30 and an outer edge 43 of main surface 26 is just enough to accommodate the width of connector clip 12.

The ends of bracing ridge 28 are preferably flat so that the ends of the bracing ridge 28 will lie flat upon inner surface 44 of the inserted spring arms 11 and 18 to provide secure and stable support. FIG. 5A is a perspective view of a female member of a housing of a connector assembly according to an embodiment of the present invention. FIG. 5B is a perspective view of the female member of FIG. 5A having a connector clip positioned thereon. FIG. 5A shows female member 14 without connector clip 12, while FIG. 5B shows female member 14 with a properly positioned connector clip 12, with support ridge 30 positioned within spring back 22, and spring arms 11 and 18 held open in a partially deflected state by bracing ridge 28. A portion of each of spring arms 11 and 18 projects over circular aperture 19 when connector clip 12 is positioned within the housing, to provide contact points for an inserted lead. It is noted that connector clip 12 may be spot welded to help retain connector clip 12 in place, or otherwise attached to the housing.

According to an embodiment of the present invention, housing 13 also includes a male member 16 that is operably connected to female member 14. FIG. 6A is a top view of a male member of a connector assembly, according to an embodiment of the present invention. FIG. 6B is a side view of a male member of a connector assembly, according to an embodiment of the present invention. FIG. 6C is a bottom, or exterior, view of a male member of a connector assembly, according to an embodiment of the present invention. As illustrated in FIGS. 6A-6C, according to one embodiment of the present invention, male member 16 is an annular disk with a wide, circular aperture 33 centered within the annular disk. In various embodiments, central aperture 33 has a diameter of approximately 0.05-0.25 inches, similar to that found in female member 14. Male member 16 is similar to female member 14, in that male member 16 includes main surface 26, supporting bracing ridge 28 and support ridge 30 running along and adjacent to central aperture 33, that have essentially the same dimensions and functions as those described above. Alternatively, bracing ridge 28 and support ridge 30 may include bracing pegs and support pegs (not shown) similar to those described above in the description of female member 14. Female member 14 includes annular shelf 24, and male member 16 includes a cylindrical rim 32 that extends outward along and perpendicular to the outer edge of main surface 26 of male member 16. Cylindrical rim 32 forms a short cylinder that encloses the components of housing 13 when the male and female members are placed together. In various embodiments of the present invention cylindrical rim 32 has an outer diameter of approximately 0.10-0.30 inches and an inner diameter of 0.05-0.35 inches, such that cylindrical rim 32 fits snugly onto annular shelf 24 of female member 14 when the two members 14 and 16 are placed together.

FIG. 7A is a perspective view of a male member of a connector assembly, according to an embodiment of the present invention. FIG. 7B is a perspective view of the male member of FIG. 7A having a connector clip positioned therein. Again connector clip 12 may be spot welded to help retain connector clip 12 in place or otherwise attach connector clip 12 to male member 16. As can be seen most clearly in FIG. 7B, a portion 45 of each of spring arms 11 and 18 projects over and within circular aperture 33 when connector clip 12 is positioned on male member 16 with support ridge 30 positioned within spring back 22 and spring arms 11 and 18 positioned in a partially deflected position by bracing ridge 28, so that portion 45 forms a contact point 34 that comes in contact with a lead (not shown) subsequently inserted within connector assembly 10.

As noted above, male member 16 and female member 14 are designed so that male member 16 and female member 14 fit together to create single housing 13 enclosing one or more connector clips 12. FIG. 8A is a side view of an embodiment of an assembled connector assembly, according to the present invention. From the side view, cylindrical rim 32 of male member 16 is visible. The only portion of female member 14 that is visible in FIG. 8A is the edge of annular shelf 24. FIG. 8B is a cross-sectional side view of the assembled connector assembly of FIG. 8A. As illustrated in FIG. 8B, within connector assembly 10, the cross-section of one connector clip 12 cuts through spring arms 118 of connector clip 12 in male member 16, while the cross section of the other connector clip 12 mounted in female member 14 shows the midpoint of spring back 22. FIGS. 8A and 8B illustrate that the assembled housing 13 creates a barrier against leakage of fluid through the connector into the apparatus. Finally, FIG. 8C is a top view of an assembled connector assembly, according to the present invention. In FIG. 8C, contact points 34 of connector clip 12 for engaging against a lead (not shown) inserted within an assembled connector assembly 10 are visible where connector clips 12 extend into aperture 19 created by housing 13, with aperture 19 of female portion 14 and aperture 33 of male portion 16 overlapping to form an opening 47 for receiving a lead with springs arms 11 and 18 of connector clip 12 in the partially deflected position. When two connector clips 12 are juxtaposed in a perpendicular fashion, as shown in FIG. 1, connector clips 12 form a square wherein the midpoint of each side of the square forms a potential contact point 34. While not required to practice the present invention, an embodiment using two, perpendicularly-placed connector clips 12 provides four contact points 34 along the four points of the compass. The placement of two perpendicular connector clips 12 helps to securely contact and retain the contact areas of a lead, as deviation of the lead in any particular direction will naturally be countered by the tension within the connector clips 12. As a result, the connector of the lead may be oriented in any direction around its central axis and function equally well.

Figure 9:
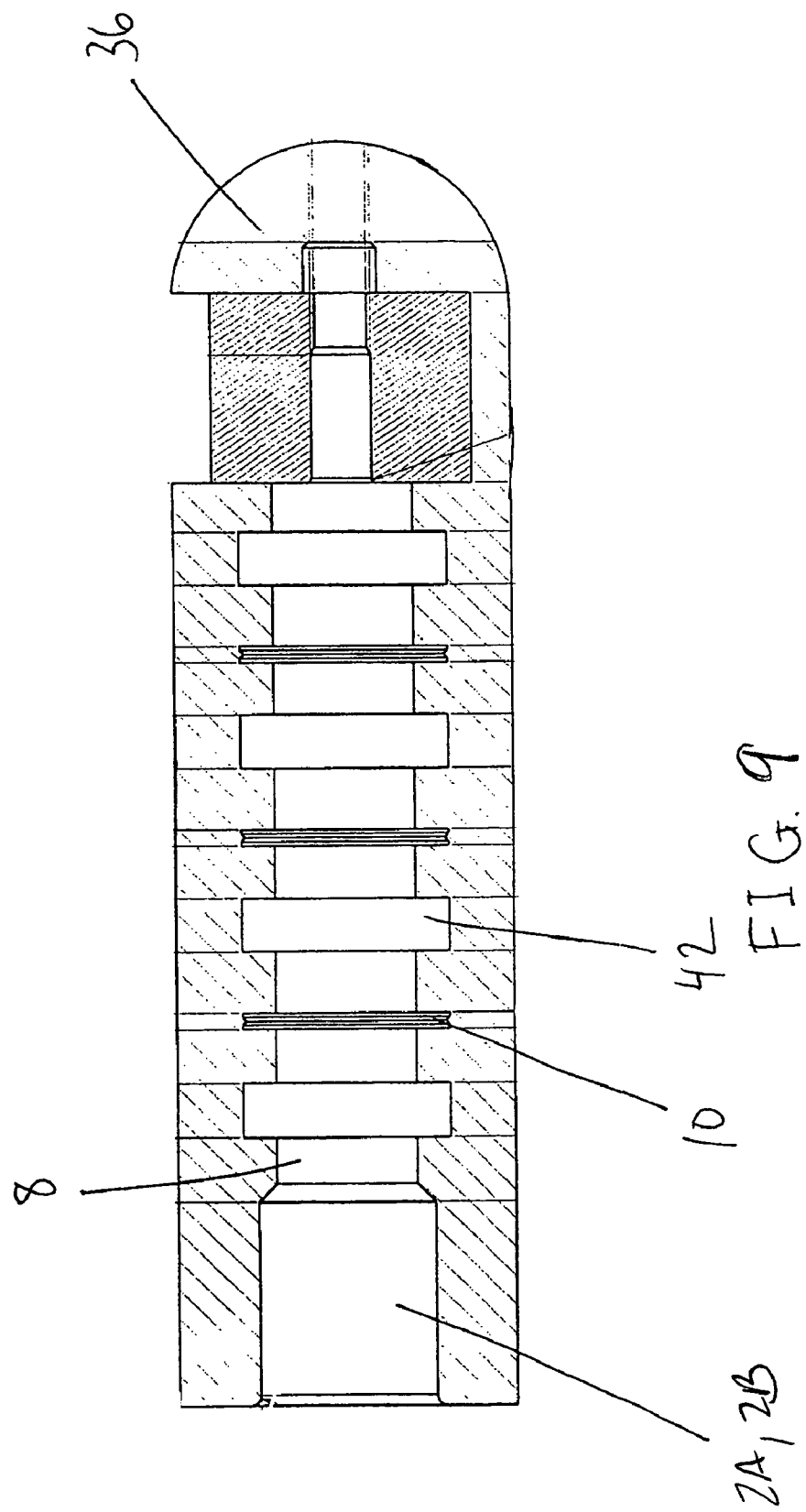

Male member 16 and female member 14 of the present invention are preferably prepared from a high strength, corrosion resistant, biocompatible material, such as tempered stainless steel. However, any conductive biocompatible material may be utilized to prepare housing 13 of the present invention. As previously suggested, housing serves to position connector clips 12 to be in a partially loaded position thereby providing for more ease in inserting the lead. Generally, housing 13 also serves to conduct electricity from connector clips 12 to another conductor (not shown), which is connected with the electrical apparatus, such as a pacemaker. FIG. 9 is a schematic diagram of a connector assembly according to the present invention inserted within a connector cavity and having a lead connector positioned there through. As illustrated in FIG. 9, housing 13 also allows connector assembly 10 to be properly positioned within a connector cavity 136, as illustrated in FIG. 9. While the FIGS. 1-10 illustrate a cylindrical, disc-shaped connector with a circular aperture, neither of these structural features are required for the present invention. For example, if it were desirable to attach a square lead, a square central aperture would be preferred. Furthermore, the overall shape of the connector assembly 10 may deviate from the cylindrical disc illustrated in FIGS. 1-10 without compromising its function.

Prior to use of the present invention, one or more connector clips 12 are placed within housing 13 and over support ridge 30 and bracing ridge 28 of one or both of female member 14 and male member 16 so that bracing ridge 28 deflects connector clips 12 in the partially deflected position, with arms 118 extending within aperture 19 (FIG. 7B), or if two clips are utilized, within both aperture 19 and aperture 33 (FIG. 8C). Prior to such placement, connector clips 12 are in a relaxed non-deflected state, in which the arms bend slightly inwards, as shown in FIG. 2. After placement, spring arms 11 and 18 of connector clips 12 are partially deflected by bracing ridge 28 thereby placing connector clip 12 in a partially loaded or deflected state so as to reduce the force required to insert the lead into connector assembly 10, with portion 45 of each spring arm 118 projecting over circular aperture 19 and circular aperture 33. After such placement of connector clip 12, connecter assembly 10 is ready to receive and retain an electrical lead.

According to the present invention, the connection of lead 2A or 2B to an electrical device may be accomplished by utilizing one or more of connector assemblies 10 of the present invention. As illustrated in FIG. 9, several of connector assemblies 10 of the present invention may be utilized within a connector cavity 36 forming a portion of connector block 7 that conforms with international standard IS-4 requirements. Use of several connector assemblies 10 provide a greater number of contact points 34, resulting in an even more secure and reliable connection to contact areas 8 of electrical lead 2A or 2B.

Whether one or more connector assemblies 10 of the present invention is utilized, each connector assembly 10 is positioned within connector cavity 36 of a connector region where connector assembly 10 is coupled with wires or other suitable means such that connector assembly 10 is in electrical communication with an electrical source (not shown). The connector region is normally constructed from plastic, silastic, or other electrically non-conductive material, and serves to position connector assembly 10 while preventing undesirable leakage of body fluids or electric current. A wire (not shown) generally runs from connector assembly 10 to the working portion of the apparatus that provides transmission of electrical current, such as electrical pulses. Examples of apparatuses for emitting electrical pulses for use with the present invention may be single or dual chamber pacemakers, antiarrhythmia pacers, defibrillators, cardiomyoplasty stimulators, neurostimulators, and other such devices which emit electrical impulses.

Figure 10:
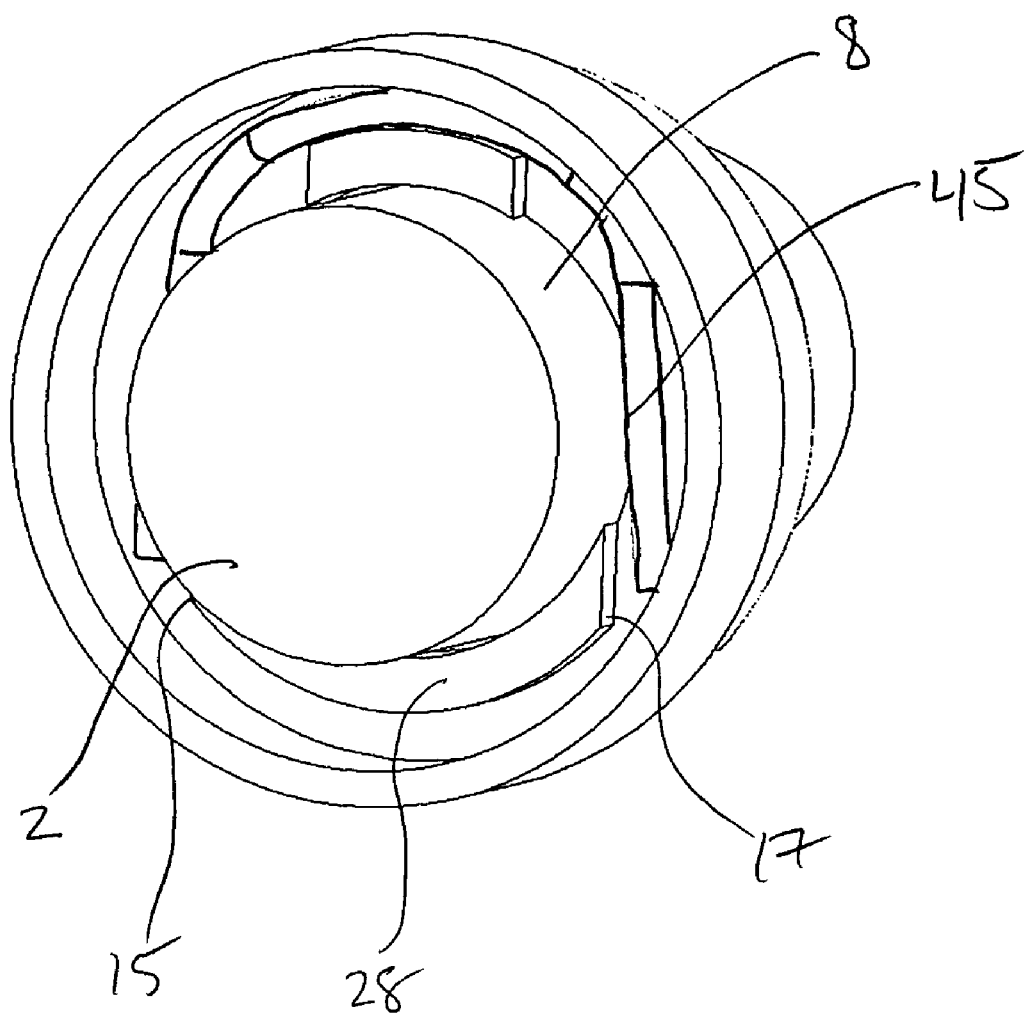
FIG. 10 is a schematic diagram of a connector assembly, according to an embodiment of the present invention with a lead inserted therein.

FIG. 10 is a schematic diagram of a connector assembly, according to an embodiment of the present invention with a lead inserted therein. As illustrated in FIGS. 9 and 10, when a physician or other user of the device wishes to establish an electrical connection between electrical lead 2A or 2B and the electrical source, the physician need merely place contact areas 8 of electric lead 2A or 2B within connector cavity 36. Contact area 8A or 8B is then urged into connector cavity 36, where contact areas 8 comes in contact with and pushes against contact points 34 of connector clip 12 of connector assembly 10 of the present invention. As lead 2A or 2B is inserted within connector cavity 36 of connector block 7, lead 2A or 2B advances through apertures 19 and 33, causing spring arms 11 and 18 of connector clip 12 to be deflected yet further from the partially deflected position, engaged against bracing ridge 28 to extend outward from and no longer engaged against ends 15 and 17 of bracing ridge 28, placing connector clip 12 in a fully deflected position. As a result, the spring force of connector clip 12 is transferred from being engaged against bracing ridge 28 to being against contact areas 8 of lead 2A or 2B. In this way, portion 45 of each spring arm 11 and 18 is engaged against contact areas 8, causing the spring force to be applied by spring arms 11 and 18 against inserted contact areas 8, creating a secure electrical connection at contact points 34. Once fully inserted, electrical lead 2A or 2B is in a loaded state and will remain in place, connected to the electrical source.

Lead 2A or 2B may optionally be provided with grooves (not shown) positioned at expected contact points 34 that serve to further secure lead 2A or 2B when connector clip 12 expands into the space of the groove. Also illustrated in FIG. 9 are several sealing devices 42, which help assure that body fluids do not leak into and possibly clog and/or corrode connector assembly 10, contact areas 8 and the electrical apparatus.

It is apparent from the foregoing discussion that the embodiments of the present invention illustrated in FIGS. 1-10 provides an improved connector assembly 10 for detachably connecting contact areas 8 of electrical lead 2A or 2B to an electrical apparatus. Since connector clips 12 are retained by housing 13 in a partially deflected configuration, a constant force is exerted over the range of deflection of connector clip 12. Furthermore, since only a small deflection is necessary to create a significant force of retention, connector assembly 10 makes efficient use of the axial space on contact areas 8, allowing it to be very compact. Connector assembly 10 readily accepts insertion of contact areas 8, without the use of tools, and applies even force through connector clips 12 to maintain a constant electrical contact with electrical lead 140 that is not subject to varying impedance.

Although the invention has been described with reference to particular embodiments, it is to be understood that such embodiments are merely illustrative of the application of the principles of the invention. Numerous modifications may be made therein, and other arrangements may be devised, without departing from the true scope and spirit of the invention.

The invention claimed is:

1. A connector assembly for detachably connecting a lead to an implantable medical device, comprising:
    a first deflectable connector clip including a first arm, a second arm, and a top portion extending between the first arm and the second arm;
    a housing having a first member and a second member, the first member having a first outer surface forming an annular shelf and the second member having a second outer surface and a cylindrical rim extending outward along and perpendicular to an outer edge of the second outer surface, the annular shelf of the first member formed to receive the cylindrical rim to be fixedly engaged with the second member to retain the first connector clip within the housing, the engaged first member and the second member forming an aperture for receiving the lead;
    a first inner surface of the first member extending from the aperture to the first outer surface and a second inner surface of the second member extending from the aperture to the second outer surface;
    a first deflection portion extending outward from at least one of the first inner surface and the second inner surface along the top portion of the first deflectable clip; and
    a second deflection portion extending outward from the at least one of the first inner surface and the second inner surface to be positioned between the first arm and the second arm, the second deflection portion deflecting the connector clip, prior to insertion of the lead between the first arm and the second arm, from a first position corresponding to a first distance between the first arm and the second arm, to a second position corresponding to a second distance between the first arm and the second arm, wherein the second distance is greater than the first distance.

2. The connector assembly of claim 1, wherein the housing and the connector clip are formed of an electrically conductive metal.

3. The connector assembly of claim 2, wherein the electrically conductive metal is stainless steel.

4. The connector assembly of claim 1, wherein the first arm and the second arm are engaged against the lead as the lead is advanced through the aperture to further deflect the first arm and the second arm from the second position to a third position.

5. The connector assembly of claim 4, wherein the second deflection portion extends between a first end and a second end, and the first arm and the second arm are engaged against the first end and the second end, respectively, when the connector clip is in the second position.

6. The connector assembly of claim 5, wherein the first arm and the second arm extend a distance outward from the first end and the second end, respectively, when the connector clip is in the third position.

7. The connector assembly of claim 1, further comprising:
    a second deflectable connector clip including a first arm, a second arm, and a top portion extending between the first arm and the second arm of the second connector clip;
    a third deflection portion extending outward from the other of the first inner surface and the second inner surface along the top portion of the second connector clip; and
    a fourth deflection portion, extending outward from the other of the first inner surface and the second inner surface to be positioned between the first arm and the second arm of the second connector clip, deflecting the second connector clip from the first position to the second position.

8. The connector assembly of claim 7, wherein the first connector clip is positioned generally perpendicular to the second connector clip.

9. The connector assembly of claim 7, wherein the first arm and the second arm of the first connector clip and the first arm and the second arm of the second connector clip are engage against the lead as the lead is advanced through the aperture to further deflect the first arm and the second arm of the first connector clip and the first arm and the second arm of the second connector clip from the second position to a third position.

10. The connector assembly of claim 1, wherein the first arm and the second arm of the first connector clip are positioned outward from the second deflection portion and the first arm and the second arm of the second connector clip are positioned outward from the fourth deflection portion when the first connector clip and the second connector clip are in the third position.

11. The connector assembly of claim 1, wherein ends of the first arm and the second arm include tapered portions to provide clearance between the ends and the housing.

12. The connector assembly of claim 1, wherein the first deflectable clip is anchored to the housing by the first deflection portion of the second member prior to insertion of the lead.

13. An implantable medical device capable of being detachably connected to a lead, comprising:
    a first deflectable connector clip including a first arm, a second arm, and a top portion extending between the first arm and the second arm;
    a housing having a first member and a second member, the first member having a first outer surface forming an annular shelf extending radially outward from an edge of a main surface and terminating at an outer edge of the first member, and the second member having a second outer surface and a cylindrical rim extending outward along and perpendicular to an outer edge of the second outer surface, the annular shelf of the first member formed to receive and fixedly engage with the cylindrical rim of the second member to retain the first connector clip within the housing, the engaged first member and the second member forming an aperture for receiving the lead;

a first inner surface of the first member extending from the aperture to the first outer surface and a second inner surface of the second member extending from the aperture to the second outer surface;

a first deflection portion extending outward from at least one of the first inner surface and the second inner surface along the top portion of the first deflectable clip; and a second deflection portion extending outward from the at least one of the first inner surface and the second inner surface to be positioned between the first arm and the second arm, the second deflection portion deflecting the connector clip, prior to insertion of the lead between the first arm and the second arm, from a first position corresponding to a first distance between the first arm and the second arm, to a second position corresponding to a second distance between the first arm and the second arm, wherein the second distance is greater than the first distance.

14. The device of claim 13, wherein the housing and the connector clip are formed of an electrically conductive metal.

15. The device of claim 14, wherein the electrically conductive metal is stainless steel.

16. The device of claim 13, wherein the first arm and the second arm are engage against the lead as the lead is advanced through the aperture to further deflect the first arm and the second arm from the second position to a third position.

17. The device of claim 16, wherein the second deflection portion extends between a first end and a second end, and the first arm and the second arm are engaged against the first end and the second end, respectively, when the connector clip is in the second position.

18. The device of claim 17, wherein the first arm and the second arm extend a distance outward from the first end and the second end, respectively, when the connector clip is in the third position.

19. The device of claim 13, further comprising:

a second deflectable connector clip including a first arm, a second arm, and a top portion extending between the first arm and the second arm of the second connector clip;

a third deflection portion extending outward from the other of the first inner surface and the second inner surface along the top portion of the second connector clip; and a fourth deflection portion, extending outward from the other of the first inner surface and the second inner surface to be positioned between the first arm and the second arm of the second connector clip, deflecting the second connector clip from the first position to the second position.

20. The device of claim 19, wherein the first connector clip is positioned generally perpendicular to the second connector clip.

21. The device of claim 19, wherein the first arm and the second arm of the first connector clip and the first arm and the second arm of the second connector clip are engage against the lead as the lead is advanced through the aperture to further deflect the first arm and the second arm of the first connector clip and the first arm and the second arm of the second connector clip from the second position to a third position.

22. The device of claim 13, wherein the first arm and the second arm of the first connector clip are positioned outward from the second deflection portion and the first arm and the second arm of the second connector clip are positioned outward from the fourth deflection portion when the first connector clip and the second connector clip are in the third position.

23. The device of claim 13, wherein ends of the first arm and the second arm include tapered portions to provide clearance between the ends and the housing.

* * * * *